United States Patent
Coyle (10) Patent No.: US 10,307,642 B1
(45) Date of Patent: Jun. 4, 2019

(54) TRAINING SYSTEM AND METHOD (71) Applicant: Sports Texas Nutrition Training Fitness, Inc., Austin, TX (US)

(72) Inventor: Edward F. Coyle, Austin, TX (US)

(73) Assignee: Sports Texas Nutrition Training Fitness, Inc., Austin, TX (US)

( * ) Notice: Subject to any disclaimer, the term of this patent is extended or adjusted under 35 U.S.C. 154(b) by 0 days.

(21) Appl. No.: 15/860,232

(22) Filed: Jan. 2, 2018

Related U.S. Application Data (60) Provisional application No. 62/585,287, filed on Nov. 13, 2017.

(51) Int. Cl.
*A61B 5/00* (2006.01)
*A61B 5/22* (2006.01)
*A63B 21/22* (2006.01)
*A63B 22/06* (2006.01)
*A63B 24/00* (2006.01)

(52) U.S. Cl.
CPC .......... *A63B 24/0062* (2013.01); *A61B 5/221* (2013.01); *A61B 5/486* (2013.01); *A61B 5/742* (2013.01); *A63B 21/225* (2013.01); *A63B 22/0605* (2013.01); *A63B 24/0075* (2013.01); *A63B 2024/0068* (2013.01)

(58) Field of Classification Search
CPC .............. A63B 24/0062; A63B 21/225; A63B 22/0605; A63B 24/0075; A63B 2024/0068; A61B 5/486; A61B 5/742; A61B 5/221
See application file for complete search history.

(56) References Cited

U.S. PATENT DOCUMENTS

| | | | | |
|---|---|---|---|---|
| 4,938,475 A | * | 7/1990 | Sargeant | A63B 21/0053 324/160 |
| 5,632,716 A | * | 5/1997 | Bui | A61N 1/36042 600/16 |
| 2005/0043145 A1 | * | 2/2005 | Anderson | A63B 22/001 482/52 |

(Continued)

OTHER PUBLICATIONS

McLean B, et. al, "Maximal power output and perceptual fatigue responses during a Division I female collegiate soccer season," 2012, 3189-3196, Journal of Strength and Conditioning Research. 26.

(Continued)

*Primary Examiner* — Sundhara M Ganesan
(74) *Attorney, Agent, or Firm* — Jeffrey D. Hunt; Hunt Pennington Kumar & Dula PLLC (57) ABSTRACT

The present disclosure provides a training method for operating a training system including a pedal-crank input unit drivingly connected in freewheeling relationship to a flywheel machine with inertial load of at least (0.5) kg·m², an ergometer to determine power, a processor, a profile module, and a session management module, wherein the processor determines a minimum acceptable threshold value of maximum power output for a maximum power period, duration of the maximum power period, and increments the minimum acceptable threshold value of maximum power output for a next maximum power period where the minimum acceptable threshold value of maximum power output for a maximum power period is met.

23 Claims, 3 Drawing Sheets

(56) References Cited

U.S. PATENT DOCUMENTS

| | | | |
|---|---|---|---|
| 2014/0106936 A1* | 4/2014 | Puerschel | A63B 21/0051 482/6 |
| 2014/0176346 A1* | 6/2014 | Brumback | A61B 5/0015 340/870.16 |
| 2015/0165271 A1* | 6/2015 | Lin | A61B 5/024 482/9 |
| 2015/0309480 A1* | 10/2015 | Patton | G04F 1/005 368/109 |
| 2015/0360083 A1* | 12/2015 | Lagree | A63B 24/0075 482/130 |

OTHER PUBLICATIONS

Coyle, E.F., et. al, "Leg extension power and muscle fiber composition," 1979, 12-15, Medicine and Science in Sports, 11.

Trinity, et. al, "Maximal Mechanical Power During a Taper in Elite Swimmers," 2016, 1643-1649, Medicine and Science in Sports and Exercise, 38.

Trinity, et, al, "Maximal Power and Performance During a Swim Taper," 2008, 500-506, International Journal of Sports Medicine, 29 (6).

Martin, J.C., et. al, "Inertial-Load Method Determines Maximal Cycling Power in a Single Exercies Bout," 1997, 1505-1512, Medicine and Science in Sports and Exercies, 29 (11).

Marlin, J.C., et. al, "Time Course of Learning to Produce Maximum Cycling Power," Feb. 2000, 485-487, Department of Kinesiology and Health Education, The University of Texas at Austin, Training and Testing.

\* cited by examiner

200 – Training System
255 – Pedal-Crank Input Unit
256 – Flywheel Machine
270 – Management Controller
274 – Profile Module
277 – System Bus
275 – Pedal-Crank Sensor
278 – Flywheel Machine Sensor
279 – Display Unit
280 – Ergometer System
282 – Session Management Module
284 – Measurement Module
286 – Processor
287 – Memory
288 – Session Timing Module
289 – Physical Conditioning Module

FIG. 3

TRAINING SYSTEM AND METHOD

CROSS-REFERENCE TO RELATED APPLICATIONS

This application is related and claims priority to U.S. Provisional Application 62/585,287 filed Nov. 13, 2017, entitled "Training System and Method", which is incorporated by reference in entirety.

FIELD OF THE INVENTION

The present disclosure relates to training methods and training systems for use in physical conditioning of individuals.

BACKGROUND OF THE INVENTION

Training methods and training systems for physical conditioning of individuals may include uncontrolled, ad hoc individual usage of training equipment such as, for example, stationary bicycles or road bicycles. Training methods and systems may include high intensity training ("HIT" training). HIT training is a form of strength training that focuses on performing exercise training repetitions to the point of momentary muscular failure typically performed over a duration of 15-45 seconds. (See, Philbin, John (2004). *High-Intensity Training; more strength and power in less time*. Human Kinetics. ISBN 978-0-7360-4820-0) One form of interval training, High-intensity interval training (HIIT), is directed to a cardiovascular exercise strategy of alternating short periods of intense anaerobic exercise with less intense recovery periods. (See Laursen P B, Jenkins D G (2002). "The Scientific Basis for High-Intensity Interval Training". *Sports Medicine* (Review). 32 (1): 53-73. PMID 11772161; See Nybo, Lars; Sundstrup, Emil; Jakobsen, Markus D.; Mohr, Magni; Hornstrup, Therese; Simonsen, Lene; Bülow, Jens; Randers, Morten B.; Nielsen, Jeers J. (2010-10-01). "High-intensity training versus traditional exercise interventions for promoting health". *Medicine and Science in Sports and Exercise*. 42 (10): 1951-1958. ISSN 1530-0315. PMID 20195181.)

BRIEF SUMMARY OF THE INVENTION

Existing training methods and training systems are characterized by various shortcomings and deficiencies. According to disclosed subject matter, the deficiencies of existing training methods and training systems may be reduced or avoided. Such reducible or avoidable deficiencies of existing training systems and methods may include, for example, limited effectiveness, variance in effectiveness, imprecision, undesirable fatigue, inconsistency, overtraining, chance of injury, poor measurement of training and productivity, and uncertainty in the objectives and effects of training activities. Particularly in view of the preceding, need exists for improvements in the field of art.

Disclosed subject matter may include a maximal power interval training method, wherein a pedal-crank input unit outputs power to a flywheel machine in a training event including a series of maximum power periods each having a duration of one (1) to ten (10) seconds, and resting periods between the maximum power periods. In embodiments, such a training method may be performed in relation to a session management module outputting a maximum power prompt from a processor to a display unit, and in relation to establishing a threshold value for the minimum acceptable value of maximum power output for the pedal-crank input unit in relation to a profile for the training session. In embodiments, a profile for the training session may be predetermined, created, or identified from a record of operations for the same machine being used in the training session, or another machine identical to the one being used in the session. In an embodiment, a training session profile for managing operation of the training system may be predetermined, identified or created for a particular individual, who may be identified as the training session user. In embodiments, the training session profile may include a user profile for a training session user. In embodiments, the profile may include a training system usage profile from a record of operation for a pedal-crank input unit, a flywheel machine, or both. Such a training method may include iteration and incremental progression of threshold values for maximal power output from the pedal-crank input unit to the flywheel machine as maximal power changes.

In embodiments, a training system may include a pedal-crank input unit in driving relationship with a freewheeling flywheel of a working flywheel machine, configured to perform a maximal power interval training method. A training system may include a session management module configured to issue outcome prompts, including success prompts and failure prompts. The session management module may increment in a progression the minimum acceptable threshold values of maximum power output from the pedal-crank input unit, the flywheel machine, or both. Duration of maximum power output periods may be increased in progression, and duration of resting periods may be reduced in progression. In embodiments, a system may include an ergometer.

BRIEF DESCRIPTION OF THE DRAWINGS

The novel features believed characteristic of the disclosed subject matter will be set forth in claims, below. The disclosed subject matter itself, however, as well as a preferred mode of use, further objectives, and advantages thereof, will best be understood by reference to the following detailed description of illustrative embodiments when read in conjunction with the accompanying drawings.

DETAILED DESCRIPTION OF ILLUSTRATIVE EMBODIMENTS

Reference now should be made to the drawings, in which the same reference numbers are used throughout the different figures to designate the same components.

It will be understood that, although the terms first, second, third, etc. may be used herein to describe various elements, these elements should not be limited by these terms. These terms are only used to distinguish one element from another element. Thus, a first element discussed below could be termed a second element without departing from the teachings of the present disclosure.

The terminology used herein is for the purpose of describing particular embodiments only and is not intended to be limiting. As used herein, the singular forms "a", "an", and "the" are intended to include the plural forms as well, unless the context clearly indicates otherwise. It will be further understood that the terms "comprises" and/or "comprising" or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Figure 1:
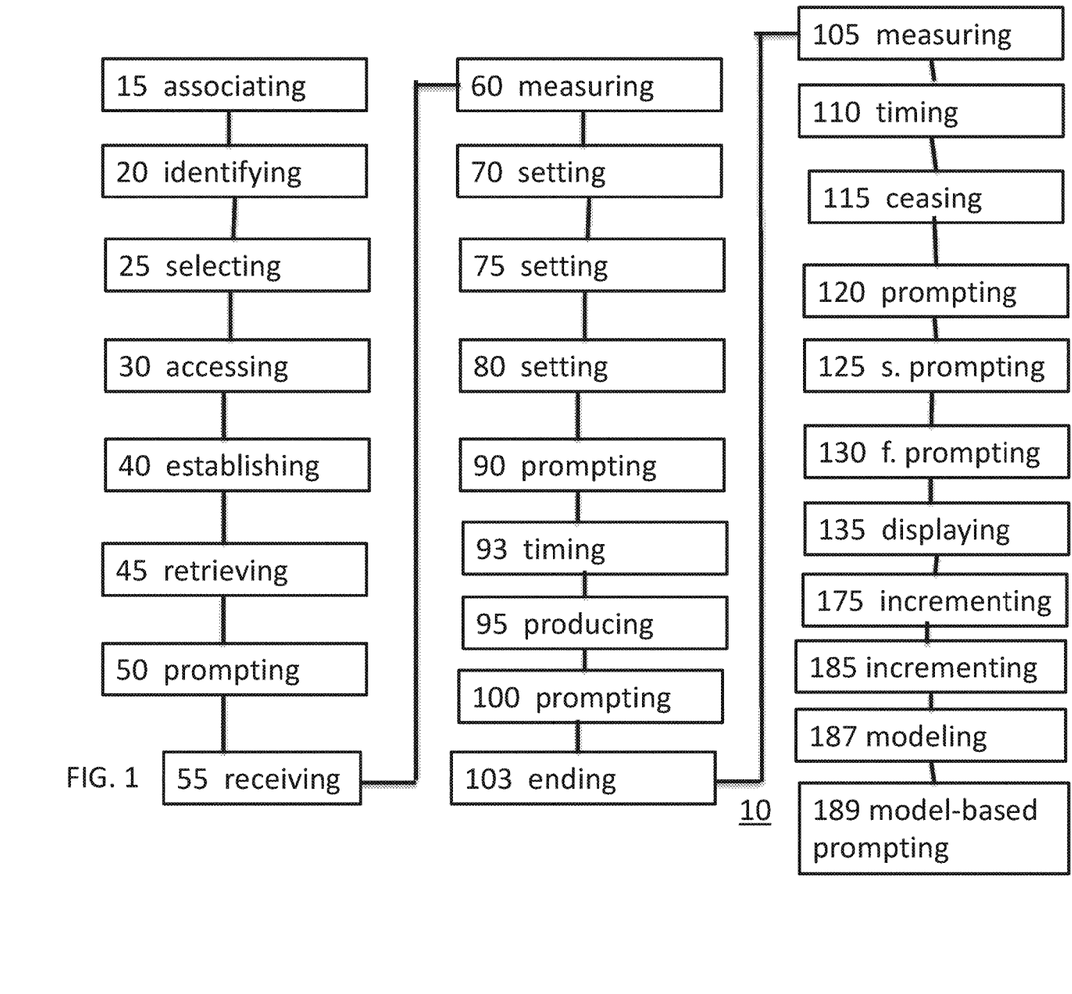
FIG. 1 is a simplified flow diagram illustrating a training method in an exemplary embodiment.
Figure 2:
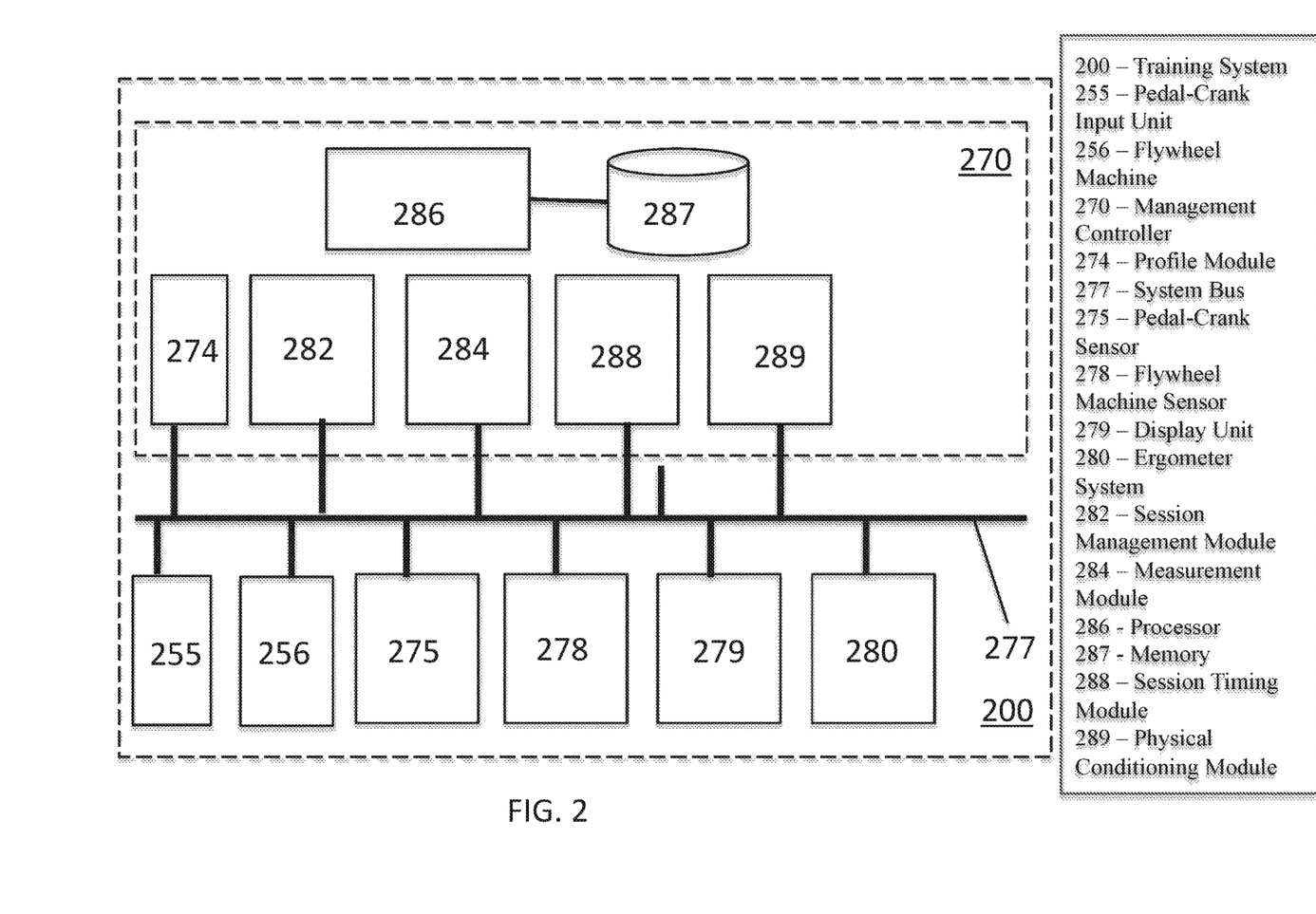
FIG. 2 is a simplified block diagram of a training system in an exemplary embodiment.

Illustrated in FIG. 1 is a simplified flow diagram illustrating a training method 10 in an exemplary embodiment. Acting as lexicographer, training method 10 is a "maximal power interval training method." The meaning and scope of "maximal power interval training method" will be understood by those of skill in the field of art upon reviewing and understanding the present disclosure. Training method 10 may be performed by operation of a training system 200 as shown in FIG. 2 and described herein. In the embodiment illustrated in FIG. 1, training method 10 may include associating 15, by a processor, a profile with a training event. A training event may encompass a training session, workout, or a group or series of alternating maximum output periods and intermediate rest periods to occur in an identifiable unit. The associating 15 may include identifying 20, by a processor, a user profile for the training event. It will be understood that a user profile may include unique user identification information and historical, recorded machine operation information for the same machine, an identical machine, or a comparable machine in a previous training event. The identifying 20 may include selecting 25 a user profile for the training event, from a plurality of user profile records in a user profile database stored in an accessible storage medium. In an embodiment, the associating 15 a profile with a training event may include accessing 30 a profile for the training event stored in an accessible storage medium, such as local or cloud storage, or a portable storage medium such as a USB type memory device, local memory of a smartphone or other smart device or IoT device, or local memory associated with processor of a training machine of a training system as further described herein.

Referring to FIG. 1, training method 10 may include initial baseline establishing 40 for initiating the training event, of an initial baseline value of maximum power output. As used herein, "maximum power output" means power output from a power input unit to a working machine. As used herein, "power input unit" means a unit operated in a repeating cycle to perform work on a working machine. In an embodiment, a "power input unit" may be, for example, a rotatable pedal-crank input unit supported for rotation about a fixed, central crank axis to perform work on a working machine such as, for example, a flywheel machine. The flywheel machine may include a set of gears trained from the pedal-crank input unit to a rotatable flywheel of a flywheel machine. The set of gears may define a gear ratio. It will be understood that a "power input unit" may be operated by an individual performing work on the power input unit, thus causing the power input unit to operate in a repeating cycle to perform work on the working flywheel machine. An individual may cause work to be performed by a power input unit, for example, by moving the power input unit in a repeating cycle with her feet, hands or other body parts. In an embodiment, an individual may cause work to be performed by a pedal-crank input unit, for example, by pedaling with her feet to rotate the pedals and crank about the crank axis in a repeating cycle, and thus to drive the working machine such as a flywheel machine. In an embodiment, an individual may cause work to be performed by a pedal-crank input unit, for example, by pedaling with her hands to rotate the pedals and crank about the crank axis in a repeating cycle, and thus to drive the working machine such as a flywheel machine. In an embodiment, information from operation of the pedal-crank input unit, and operation of the flywheel machine, during a training event may be monitored and recorded in a training session record for the training system. A training session record for operation of the training system may be recorded in memory accessible by the processor. The training session record for operation of the training system may be accessed by the processor, for example, for the processor to establish operating data for initiating and managing operation of the training system in another training session. It will be understood that, in the other training session, the processor may access a training session record for operation of the same training system, an identical training system, or a comparable training system. The training session record may pertain to operation of a training system in a training event for the same training session user, or for a hypothetical training session user having specified performance capabilities. In an embodiment, a training session record may be created for reference by a processor in managing operation of a training system according to performance parameters selected for a composite training session user by reference to a plurality of training session records for a plurality of training session users.

In an embodiment shown in FIG. 1, the initial baseline establishing 40 may include retrieving 45 recorded machine operation information of a previous training event, for the user profile, and establishing the initial baseline value of maximum power output at a historical, recorded value of maximum power input to the machine in a previous training event in the recorded machine operation information for the user profile.

In an embodiment, the initial baseline establishing 40 may include initial baseline prompting 50 in an interface by the processor. The initial baseline establishing 40 may include receiving 55 initial baseline information input from the interface, responsive to the initial baseline prompting 50. A user associated with the training event being initiated may enter initial baseline information input via the interface, responsive to the initial baseline prompting 50. In such an embodiment, the initial baseline value of maximum power output may be set at the value received from the interface for the user who is present to participate in the training event being initiated.

In an embodiment, the initial baseline establishing 40 may include initial baseline measuring 60 of initial operation of the power input unit during an initial baseline output period, responsive to the individual causing operation of the power input unit during the baseline output period. In such an embodiment, the initial baseline value of maximum power for initiating the training event may be set to the value determined for initial baseline measuring 60 of work performed in operation of the power input unit during the baseline output period. It will be understood that operation of the power input unit is responsive to work performed by the individual to cause operation of the power input unit.

Thus, in an embodiment shown in FIG. 1, training method 10 may include threshold setting 70 of an acceptable minimum value for maximum power output for initiating the training event, at the initial baseline value identified by the initial baseline establishing 40. The initial baseline value of maximum power output for the training event may be used to determine an initial threshold for the acceptable minimum value of maximum power output for the training event.

In an embodiment shown in FIG. 1, training method 10 may include maximum power duration setting 75 of an acceptable minimum value for duration of maximum power periods wherein the acceptable minimum value for maximum power output for initiating the training event is to be produced, as provided by the threshold setting 70. In embodiments, an acceptable minimum value for duration of maximum power periods may be from 1 to 10 seconds.

In an embodiment shown in FIG. 1, training method 10 may include rest duration setting 80 of an acceptable value for initial rest duration for rest duration periods occurring between maximum power periods. The initial time of a rest duration period may be determined, for example, by using the initial threshold for the acceptable minimum value of maximum power output for the training event. In an embodiment, a rest duration may be otherwise provided.

In an example, the duration of a power period for outputting maximum power output at or exceeding the threshold minimum baseline value may be, for example, 4 seconds, while the rest duration may be, for example, 30 seconds. In an example, a training event may include a series of 30 power periods and 30 resting periods between power periods.

Training method 10 may include maximum power prompting 90, wherein the processor may issue a maximum power prompt via a visual or audio interface. Method 10 may include maximum power producing 95, wherein the power input unit may output maximum power in response to the maximum power prompting 90. It will be understood that by the maximum power prompting 90, the user is prompted to provide and direct her maximum power output into operating the power input unit. For example, responsive to the maximum effort prompting 90, the power input unit may receive from the user by her efforts, her maximum possible power output applied to cause operation of the power input unit in relation to the user power input. For example, where the power input unit is a pedal-crank input unit, the maximum power prompting 90 may cause, request or require the user to immediately pedal as hard as she can to cause the pedal-crank unit to operate and output power to the working unit at maximum power during the duration of the power period. So, in an example, the pedal-crank input unit may be caused to operate at maximum power for a power period duration of 4 seconds, in relation to maximum power prompting 90. In an example, the pedal-crank input unit may be caused to operate at maximum power for a power period duration in the range from 1 second to 10 seconds, in relation to maximum power prompting 90.

Training method 10, as shown in FIG. 1, may include power measuring 105 during the power period. Power measuring 105 may be performed, for example, by an ergometer system. In one embodiment, power may be measured or calculated as work performed by the working machine including the flywheel inertial load, where resistance is provided solely by the moment of inertia of the flywheel and the gear ratio of the set of gears trained between the flywheel and the pedal-crank. It will be understood that, in this exemplary embodiment, load due to friction may be considered de minimus. Power may be calculated as the product of angular velocity and angular acceleration and moment of inertia of the system (i.e.; the flywheel inertia and gear ratio compromise the flywheel machine), where the flywheel angular velocity and angular acceleration may be determined by operation of a sensor, such as an optical sensor or laser scanner sensor or accelerometer in communication with a processor and memory combination to provide sensor data to the same. Such a processor and memory combination may be provided, for example, in a controller. In an example, total inertia of the training system may be the product of the flywheel inertia and gear ratio provided by the set of gears trained between the pedal-crank input unit and flywheel. For example, flywheel inertia may be the product of $0.90 \text{ kg} \cdot \text{m}^2 \times 4.0 = 3.6 \text{ kg} \cdot \text{m}^2$. In this particular example, each one revolution of the pedals turns the flywheel 4.0 times (the gear ratio). The gear ratio may vary.

In an exemplary embodiment, power measuring 105 may include instantaneous calculation of power in relation to sensor data collected in relation to time measured in microseconds, such as calculation of power instantaneously for each one (1) degree of rotation of the pedal-crank of the pedal-crank power input unit, or averaged over one complete revolution of the pedal-crank. Values for maximum power output from the pedal-crank power input unit may be identified in the power period. Within the power period, occurrence and duration of compliance, and non-compliance, with the minimum acceptable threshold value of maximum power output, may be identified.

As shown in FIG. 1, training method 10 may include power period timing 93 by a power period timer initiated and controlled by the processor, where the power period timer under control of the processor is set to run for the power period duration and then expire to end the power period. Training method 10 may include initiating the power period timer once the instantaneous power output exceeds the initial minimum acceptable threshold value of power output. It will be understood that the initial minimum acceptable threshold value of power output may be the initial minimum acceptable threshold value of the maximum power output. The time period between issuance of the maximum power output prompt and that time at which the instantaneous power output reaches the threshold of initial minimum acceptable value of maximum power output, may be considered a ramp up period. Method 10 may include resting period prompting 100 by the processor wherein the processor may issue a resting period prompt via a visual or audio interface. Method 10 may include resting period ending 103, wherein the power input unit may output no power, or less than threshold power, in response to the resting period prompting 100. It will be understood that by the resting period prompting 100, the user is prompted to cease providing her maximum power output. Resting period prompting 100 to the user, instructing the user to rest, may be accompanied by the processor initiating a resting period timing 110 with a duration equal to the rest duration provided by the rest duration setting 80.

Method 10 may include ceasing 115 of power output by the power input unit to the working machine. During the resting period duration of the rest timer the power input unit may receive significantly reduced, or no power, from the individual being trained in the training event. Method 10 may include outcome dependent prompting 120 by the processor via the audio or visual interface, after expiration of the power period and timer, to communicate a prompt in relation to the outcome of instantaneous power output during the duration of the power session timer. Output dependent prompting 120 may include success prompting 125 issued by the processor via the interface where the instantaneous power output is greater than or equal to the threshold minimum acceptable value of the maximum power output during the duration of the power period. Output dependent prompting 120 may include failure prompting 130 issued by the processor via the interface where the instantaneous power output falls below the threshold minimum acceptable value of the maximum power output during the duration of the power period. Output dependent prompting 120 may include displaying 135 of an outcome report, caused by the processor via the interface to communicate the instantaneous power output during the duration of the effort timer.

In embodiments, the combined series of a power period and subsequent rest period, running between the issuance of a maximum power prompt by maximum power prompting 90 and the subsequent expiration of a resting period timer by resting period prompting 100, may be considered one power period—resting period "cycle". A cycle in which a success notification is issued by success prompting 125 is (i.e. where instantaneous power output is maintained at or above the minimum acceptable threshold value of acceptable maximum power output during the power session duration of the power period timer) may be considered a success cycle. A cycle in which a failure notification is issued by failure prompting 130 (i.e. where instantaneous power output falls below the acceptable max power output threshold at some point during the duration of the effort timer) may be considered a failed cycle. A combined plurality of cycles (ramp up period, maximum power periods, and reduced power periods, along with associated prompts and reports issued by the system) may form a training event. A training event may consist of a number (n) of cycles, or may consist of a number (n) of success cycles.

As shown in FIG. 1, training method 10 may include progression incrementing 175 of at least one of the minimum acceptable threshold value for maximum power output and the maximum power output period duration, responsive to satisfactory performance of the power input unit. For example, progression incrementing 175 may occur by the processor causing to be provided to the audio or video interface a progressive incremented threshold value, power period duration, or both, where the preceding minimum acceptable threshold value for maximum power output has been met by the power input unit for the complete duration of the preceding maximum power output period duration, such as in one or more consecutive number (n) of cycles or with predetermined frequency.

As shown in FIG. 1, training method 10 may include peak progression incrementing 185 of the minimum acceptable threshold value for maximum power output, responsive to each new peak operation of the power input unit. For example, peak progression incrementing 185 may occur by the processor causing to be provided to the audio or video interface a progressive incremented threshold value, where the power input unit has performed a new peak operation in a power period that also exceeds the minimum acceptable threshold value for maximum power output for the complete duration of the corresponding maximum power output period duration. Peak progression incrementing 185 also may include incrementing the corresponding power period duration for operation of the power input unit at the progressive incremented minimum acceptable threshold value for maximum power output, by the processor causing to be provided to the audio or video interface a progressive incremented power period duration for expiration of the power period timer.

Training method 10 may include increasing at least one of the minimum acceptable threshold value of maximum power output and maximum power output duration of the power period. Training method 10 may include iterating the increasing of at least one of the minimum acceptable threshold value of maximum power output and maximum power output duration of the power period.

In embodiments, training method 10 may include the prompting 50, 90, 100, 120, 125, 130 being determined or conducted in relation to generating and presenting by the processor, via the interface, a prompt or a series of spaced maximum effort period prompts and resting period prompts that are timed, spaced apart, and determined by reference to a physical conditioning model. In embodiments, training method 10 may include modeling 187. Modeling 187 may include accessing a physical conditioning model. Accessing 187 may include determining or constructing a physical conditioning model by reference to operation records of a pedal-crank input unit, flywheel machine, or both, which operated during the performing of a training method in a previous training session. Modeling 187 also may include referencing physiological response records for the performing of a training method in a previous training session. In an embodiment, modeling 187 may include both referencing operations of a pedal-crank input unit, flywheel machine, or both, and also referencing physiological response records. Modeling 187 may include reference to operation records, and physiological response records, in a plurality of operation records for multiple training sessions for a plurality of individuals, or for an individual user.

Training method 10 may include model-based prompting 189 by generating and presenting by the processor, via the interface, a prompt or a series of spaced maximum effort period prompts and resting period prompts that are timed, spaced apart, and determined by reference to a physical conditioning model. In embodiments, the physical conditioning model may be selected, determined or constructed by reference to operation records for performing a training method in a previous training session, or may be compiled by reference to a plurality of operation records for multiple training sessions. In embodiments, the physical conditioning model may be selected, determined or constructed by reference to operation records of a pedal-crank input unit, flywheel machine, or both, which operated during the performing of the same training method in a previous training session. In some embodiments, the physical conditioning model may be selected, determined or constructed by reference to operation records of a pedal-crank input unit, flywheel machine, or both, which operated during the performing of the same training method by the same individual user in a previous training session. In some embodiments, the physical conditioning model may be selected, determined or constructed by reference to a plurality of operation records of a pedal-crank input unit, flywheel machine, or both, which operated during the performing of the same training method by a plurality of individual users in a previous training session. In embodiments, the modeling 187 and model-based prompting 189 may provide the spaced prompts in correspondence with model values of a physical conditioning model or physiological response model, and may be determined according to such a model as model values for stimulating maximal activation of a muscle and nervous system of a model individual. It will be understood that the physical conditioning model or physiological response model, for example, may relate to a composite model determined for a plurality of individuals, or a model of a particular individual user.

In an embodiment, training method 10 may include, in the modeling 187, the physical conditioning model or physiological response model, accessing or providing a range model for training a set of exercising muscles throughout a range of the force (torque) vs. velocity curve for the pedal-crank input unit or flywheel machine. The range model may include a model for operating the pedal-crank input unit or flywheel machine, beginning from a dead stop and accelerating to a maximum RPM value. The range model may include a model for accelerating the pedal-crank input unit or flywheel machine through a range of low velocities (e.g.; 0-60 RPM) where torque is relatively high and demands strength in relation to the physical conditioning model or physiological response model. In an embodiment, the range model may include a model for accelerating the pedal-crank input unit or flywheel machine from a range of low velocities (e.g.; 0-60 RPM) through a range of mid-range velocities (60-150 RPM). A maximal power event or point may be identified in the mid-range velocities (60-150 RPM). Such a maximal power event may be identified in relation to a physical conditioning model or physiological response model, as being significant for muscle development in relation to an individual or in relation to the model. In an embodiment, the range model may include a model for accelerating the pedal-crank input unit or flywheel machine from a range of mid-range velocities (60-150 RPM) into or through a range of high velocities (e.g.; above 150 RPM). A maximal speed event or point may be identified in the range of high velocities (e.g.; above 150 RPM). Such a maximal speed event may be identified in a relation to a physical conditioning model or physiological response model, as being significant for development of coordination in relation to an individual user or in relation to the model. At velocities above 150 RPM, maximal speed may be achieved, which may serve improved coordination. In an embodiment, in training method 10 in a single short sprint it may possible, in relation to a physical conditioning model or physiological response model, to train for strength, power and coordination. In an embodiment, in training method 10 in a single short sprint it may possible to train for strength, power and coordination in relation to an individual user or in relation to a physical conditioning model or physiological response model.

In an embodiment, training method 10 may include, in the modeling 187, the physical conditioning model or physiological response model, accessing or providing a range model for training to stimulate cardiovascular adaptations. Such cardiovascular adaptations may have been previously thought possible only with long duration low intensity exercise (e.g.; running or cycling>30 min at 60-75% maximal oxygen consumption, $VO_2max$). In an embodiment, training method 10 may be a form of 'high intensity interval training' (i.e.; HITT). In fact, training method 10 may embody the highest possible type of HIIT, because the individual user may be prompted to provide maximum exertion in a sprint for a maximum power period having duration from 1-10 seconds of sprinting. In an embodiment, training method 10 may include in the modeling 187, the physical conditioning model or physiological response model, in a maximum power period the individual user causing the pedal-crank input unit to operate and generate power that is 3-6 times higher than power that elicits $VO_2max$ in the physical conditioning model or physiological response model or for an individual user. In an embodiment, in the physical conditioning model or physiological response model or for an individual user, a modeled condition or actual condition may exist wherein, in order for the exercised muscles to recover energy stores after a maximal effort period, the cardiovascular system may be stimulated to increase oxygen delivery and utilization by the muscles, by increasing heart rate and blood flow. In an embodiment, for example, in the physical conditioning model or physiological response model or for an individual user, a modeled condition or actual condition may exist wherein two (2) minutes duration of a resting period may be sufficient for recovery with relatively low stress on the cardiovascular system. In an embodiment, training method 10 may include, in the physical conditioning model or physiological response model, or for an individual user, a modeled condition or actual condition may exist wherein, progression of resting period durations between 60 seconds, 45 seconds, 30 seconds, and 15 seconds, may place or may be determined to correspond to relatively more stress on the cardiovascular system as measured by grades increases in oxygen consumption, heart rate and muscle oxygen desaturation in the physical conditioning model or physiological response model, or for an individual user. In an embodiment, by accurately controlling the resting period durations between the series of maximal effort periods, it may be possible to stimulate the cardiovascular system to provide significant aerobic improvements. In embodiment, such improvement may be achieved with only 15 minutes of total time for each training session that involves only 1-2 minutes of actual exercise. For example, if a person performs in maximum effort periods each having a duration of 4 seconds, and each of the maximum effort periods is separated by a resting period having a 30 second duration for recovery between maximum effort periods, in a 15 minute training session the individual user will have performed 26 maximum effort periods with combined duration of 104 seconds. In embodiments, training method 10 may be progressive in reduction of resting period durations in relation to the physical conditioning model or physiological response model, or for an individual user, to provide conditions corresponding to relatively more stress on the cardiovascular system as measured by graded increases in oxygen consumption, heart rate and muscle oxygen desaturation in the physical conditioning model or physiological response model, or for an individual user, and thus improve aerobic conditioning.

In embodiments, training method 10 may provide progressive improvement of muscular performance with increasing maximal power events or points, and progressive improvement of cardiovascular performance over period of multiple training sessions in relation to progressively shorter resting period durations between maximal power periods (i.e.; progressively reduced from 60, 45, 30 and to 15 seconds).

FIG. 2 is a simplified block diagram illustrating training system 200 in an exemplary embodiment. Training system 200 may be configured to perform the training method 10, as illustrated in FIG. 1 and described hereinabove. In the embodiment illustrated in FIG. 2, training system 200 may include a management controller 270 having a processor 286 associated with memory 287 accessible by the processor 286, and a plurality of function modules. The management controller 270 is in communication with system bus 277 for processing, execution and controlling of modules, and for communicating data between management controller 270 and modules, of training system 200. Training system 200 may include pedal-crank input unit 255 connected in driving relationship with a working flywheel machine 256 having a freewheeling flywheel. In embodiments, the freewheeling flywheel machine (including flywheel and gearing between the freewheeling flywheel and pedal-crank input unit) may have an inertial load with a moment of inertia of at least one (1) kg·m². In an embodiment, the flywheel alone may have a moment of inertia in the range of one-quarter (0.25) to two (2) kg·m². In embodiments, for example, training system 200 may include a flywheel having a weight of at least forty (40) pounds, a moment of inertia of 0.8 kg·m² and a gear ratio of at least 3.5:1 between the freewheeling flywheel and pedal-crank input unit. The freewheeling flywheel does not apply an opposite load on an individual user when slowing or stopping cycling. This may avoid or reduce muscle stretching, injury, and fatigue, and may improve safety in using the training system 200.

Training system 200 may include a pedal-crank sensor 275 configured to monitor rotating operation of pedal-crank input unit 255. Training system 200 may include a flywheel machine sensor 278 configured to sense or monitor rotating operation of flywheel machine 256. Training system 200 may include a display unit 279 in communication with management controller 270 over system bus 277 for displaying information regarding operation of training system 200. Display unit 279 may include an interface having visual, audio and other sensory display interface elements. Display unit 279 may include input elements for receiving information at the user interface.

Training system 200 may include a profile module 274, executable by processor 286, that may be selectable to be associated with a training event of the training system 200. As explained above, a training event may encompass operation or usage of the training system 200 during a training session, workout, or a group or series of alternating maximum output periods and intermediate rest periods to occur in an identifiable workout event unit. Training system 200 may include the profile module 274 identifying a training system usage profile for execution of the training event. A training system usage profile may include, for example, an individual user profile, for execution in the training event. As previously explained, an individual user profile ("user profile") may include unique user identification information and historical, recorded machine operation information for the same training machine, an identical machine, or a comparable machine in a previous training event. Training system 200 may include selection, by the processor 256, of a user profile for an individual for the training event, from a plurality of user profile records in a user profile database. In an embodiment, the profile module 274 may associate a profile with a training event by accessing a profile for the training event stored in memory 287 accessible by processor 286. Memory 287 may include, for example, an accessible storage medium, such as local or cloud storage, or a portable storage medium such as a USB type memory device, local memory of a smartphone or other smart device or IoT device, or local memory associated with a processor of training system 200, as further described herein.

Referring to FIG. 2, training system 200 may include the profile module 274 establishing an initial baseline for initiating the training event, of an initial baseline value of maximum power output. As used herein, "maximum power output" means a maximum amount or rate of power output from a power input unit to a working machine. As used herein, "power input unit" means a unit operated in a repeating cycle to perform work on a working machine. In an embodiment shown in FIG. 2, a "power input unit" may be, for example, a rotatable pedal-crank input unit 255 supported for rotation about a fixed, central crank axis to output power and perform work on a working machine such as, for example, the flywheel machine 256 connected in driven relationship with pedal-crank input unit 255. It will be understood that a "power input unit" may be operated by an individual performing work on the power input unit, thus causing the power input unit to operate in a repeating cycle to perform work on the working machine. An individual may cause work to be performed by a power input unit, for example, by moving the power input unit in a repeating cycle with her feet, hands or other body parts. In an embodiment, an individual may cause work to be performed by pedal-crank input unit 255, for example, by pedaling with her feet to rotate the pedals and crank about the crank axis in a repeating cycle, and thus repeating, cyclical rotating operation of the pedal-crank input unit 255 to operate to drive rotation of the working flywheel machine 256 connected in driven relationship with the pedal-crank unit 255 to receive power from the same. In an embodiment, an individual may cause work to be performed by a pedal-crank unit 255, for example, by pedaling with her hands to operate the pedals and rotate the crank about the crank axis in a repeating cycle, and thus to drive the working machine such as a flywheel machine 256 connected in driven relationship with the pedal-crank unit 255.

In an embodiment, the profile module 274 may establish the initial baseline may include retrieving recorded machine operation information of a previous training event, for the user profile, and establishing the initial baseline value of maximum power output at a historical, recorded value of maximum power input to the flywheel machine 256 from the pedal-crank input unit 255 in a previous training event recorded in the recorded machine operation information for the user profile.

In an embodiment, the profile module 274 may establish the initial baseline by the processor 286 sending an initial baseline prompt to the user interface of the display unit 279. Establishing the initial baseline may include the profile module 274 receiving initial baseline information input from the interface of display unit 279, responsive to the initial baseline prompting. A user associated with the training event being initiated may enter initial baseline information input via the user interface, responsive to the initial baseline prompting. In such an embodiment, the initial baseline value of maximum power output may be set at the value received from the interface for the user who is present to participate in the training event being initiated.

In an embodiment, the profile module 274 may establish the initial baseline by measuring initial operation of the pedal-crank input unit 255 during an initial baseline output period where the individual being trained causes operation of the pedal-crank input unit 255 during the baseline output period. In such an embodiment, the initial baseline value of maximum power for initiating the training event may be set to the value determined for measuring initial baseline of work performed on the flywheel machine 256 by operation of the power input unit 255 during the baseline output period. It will be understood that operation of the power input unit 255 is responsive to work performed by the individual being trained causing operation of the power input unit 255.

In the embodiment shown in FIG. 2, training system 200 may include a session management module 282 for determining, setting and controlling elements of each training session. Session management module 282 may set a threshold that is an acceptable minimum value for maximum power output from the pedal-crank input unit 255 for initiating the training event, at the initial baseline value identified and established by the profile module 274. The initial baseline value of maximum power output for the training event may be used to determine an initial threshold for the acceptable minimum value of maximum power output for the training event.

As shown in FIG. 2, training system 200 may include the session management module 282 setting maximum power duration of an acceptable minimum value for duration of maximum power periods in a training session, wherein the acceptable minimum value for maximum power output from pedal-crank input unit 255 for initiating the training event is provided by the threshold setting.

In an embodiment shown in FIG. 2, training system 200 may include session management module 282 setting rest duration of an acceptable value for initial rest duration for rest duration periods occurring between maximum power periods. The initial time of a rest duration period may be determined, for example, by the session management module 282 using the initial threshold for the acceptable minimum value of maximum power output for the training event.

In an example, the session management module 282 may set duration of a power period for outputting maximum power output at, or exceeding, the threshold minimum baseline value that, for example, may be 4 seconds. The session management module 282 may set the rest duration, for example, at 30 seconds. In an example, a training event may include a series of 30 power periods and 30 resting periods between power periods.

Training system 200 may include the session management module 282 performing maximum power prompting, wherein the processor may issue a maximum power prompt via the interface of display unit 279. Session management module 282 may evaluate producing of maximum power from the pedal-crank input unit 255 in relation to issuing the maximum power prompting from the interface of display unit 279. The maximum power prompting may issue a prompt, request or instruction from display unit 279. Responsive to issuance of the prompt by session management module 282 via display unit 279, the pedal-crank input unit 255 may receive from the training session user, her maximum power output to cause corresponding maximum power operation of the pedal-crank input unit 255. For example, responsive to session management module 282 issuing the maximum power prompt, the pedal-crank input unit 255 may receive from the user by her maximum efforts, her corresponding maximum power output applied to cause operation of the pedal-crank input unit 255 in relation to the training session user power input to same. Where the power input unit is a pedal-crank input unit 255, the prompt for maximum power may cause, request or instruct the training session user to immediately pedal as hard as she can at that time, to cause corresponding operation of the pedal-crank input unit 255 to output power to the working flywheel machine 256 at maximum power during the duration of the power period. So, in an example, responsive to the session management module 282 issuing a maximum power prompt via the interface of display unit 279, pedal-crank input unit 255 may operate at maximum power output in relation to maximum power input from the training session user, for a power period duration of 4 seconds.

Figure 3:
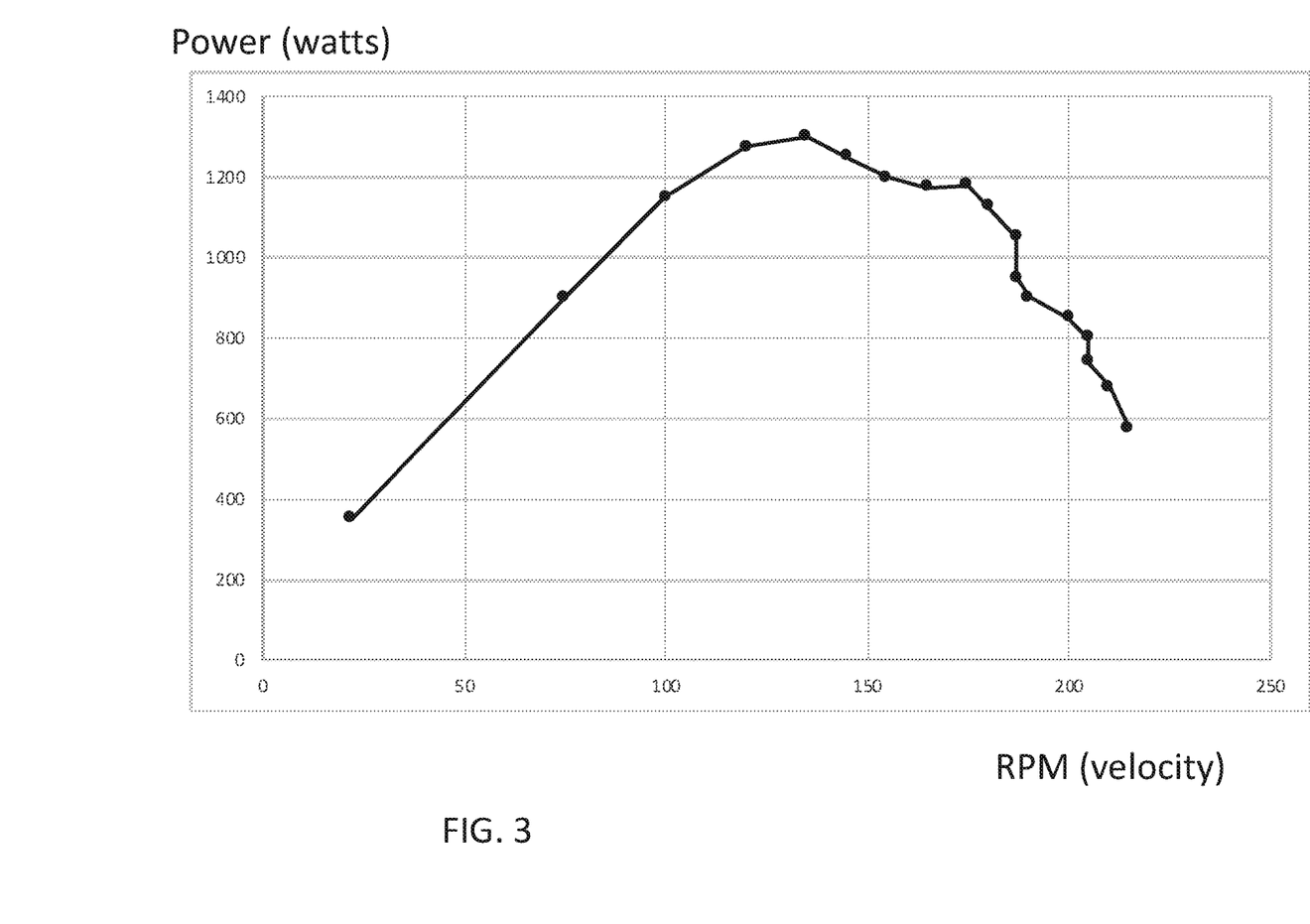
FIG. 3 shows a chart of power output in relation to velocity (revolutions per minute (RPM)) of a cycle crank connected to drive a flywheel for a training system in an exemplary embodiment.

Training system 200 may include measurement module 284 for measuring power output from pedal-crank input unit 255 during the power period. Measurement module 284 may perform power measuring, for example, by an ergometer system 280. In one embodiment, measurement module 28? may measure power or may calculate power in relation to work performed by the working flywheel machine 256. Operation of the flywheel machine 256 may include the flywheel inertial load, where resistance is provided solely by the moment of inertia of the flywheel machine. It will be understood that, in this exemplary embodiment, load due to friction may be considered de minimus. Measurement module 28 may calculate power as the product of angular velocity and angular acceleration of the flywheel, where the flywheel angular velocity and angular acceleration may be determined by operation of flywheel machine sensor 278. Flywheel machine sensor 278 may include, for example, an optical sensor or laser scanner sensor, or accelerometer in communication with a processor and memory combination to provide sensor data to the same. In the exemplary embodiment shown in FIG. 2, measurement module 284 may perform instantaneous calculation of power in relation to sensor data collected in relation to time measured in microseconds. In an example, measurement module 284 may perform instantaneous calculation of power in relation to sensor data collected in relation to time measured in microseconds, wherein power may be calculated instantaneously for each three (3) degrees of rotation of the pedal-crank of the pedal-crank input unit 255, or averaged over one complete revolution of the pedal-crank. Values for maximum power output from the pedal-crank input unit 255 to the flywheel machine 256 may be identified in the power period. FIG. 3 shows a chart of power output in relation to rotation (revolutions per minute (RPM)) of the pedal-cranks in an exemplary embodiment. As shown in FIG. 2, session management module 282 may monitor and identify, within each power period, occurrence and duration of compliance, and non-compliance, in relation to the minimum acceptable threshold value of maximum power output.

Training system 200 may include session timing module 288 for timing each power period. Session timing module 288 may include a power period timer initiated and controlled by the processor 286, where the power period timer under control of the processor 286 is set to run for the power period duration and then expire to end the power period. Training system 200 may include session timing module 288 initiating the power period timer once the instantaneous power output exceeds the initial minimum acceptable threshold value of maximum power output. The time period between issuance of the maximum power output prompt and that time at which the instantaneous power output reaches the threshold of initial minimum acceptable value of maximum power output, may be considered a ramp up period.

Training system 200 may include the session management module 282 performing resting period prompting, wherein the processor 286 may issue a resting period prompt via the interface of display unit 279. Responsive to the resting period prompting 100, in the resting period the pedal-crank input unit 255 may output no power, or may output less than threshold power, to the flywheel machine 256. The resting period prompting may cause, prompt or instruct the user to cease providing her maximum power output to the pedal-crank input unit 255. The session management module 282 may include, via the processor, causing the session timing module 288 to initiate resting period timing with a duration equal to the rest duration provided by setting the rest duration.

Training system 200 may include the pedal-crank input unit 255 ceasing power output to the working flywheel machine 256 during the resting period. During the resting period duration set by the session management module 282, the pedal-crank input unit 255 may receive significantly reduced, or no input power, from the training session user. The session management module 282 may issue outcome dependent prompts, by the processor via the interface of the display unit 279, after expiration of the power period and timer. The session management module 282 may issue outcome dependent prompts to communicate such prompts in relation to the outcome of instantaneous power output during the duration of the power session timer. The output dependent prompts may include a success prompt issued by the processor 286 via the interface of display unit 279 where the instantaneous power output is greater than or equal to the threshold minimum acceptable value of the maximum power output during the duration of the power period. The output dependent prompts may include a failure prompt issued by the processor 286 via the interface of display unit 279, where the instantaneous power output falls below the threshold minimum acceptable value of the maximum power output during the duration of the power period. The session management module 282 may issue output dependent prompts including an outcome report displayed via display unit 279, by the processor, to communicate the instantaneous power output during the duration of the effort timer.

In embodiments, the combined series of a power period and subsequent rest period, running between the issuance of a maximum power prompt and the subsequent issuance of a resting period prompt upon expiration of a resting period timer, may be considered one "power period-resting period cycle." A cycle wherein a success prompt is issued (i.e. where instantaneous power output is maintained at or above the minimum acceptable threshold value of acceptable maximum power output during the power session duration of the power period timer) may be considered a success cycle. A cycle in which a failure prompt is issued (i.e. where instantaneous power output falls below the acceptable max power output threshold at some point during the duration of the effort timer) may be considered a failed cycle. A combined plurality of cycles (ramp up period, maximum power periods, and reduced power periods, along with associated prompts and reports issued by the system) may form a training event. A training event may consist of a number (n) of cycles, or may consist of a number (n) of success cycles or may consist of a set duration.

As shown in FIG. 2, training system 200 may include session management module 282 incrementing a progression of at least one of the minimum acceptable threshold value for maximum power output and the maximum power output period duration, responsive to satisfactory performance of the power input unit. For example, session management module 282, by the processor, may cause a progressive incremented threshold value, power period duration, or both, to be provided via the interface of display unit 279 where the preceding minimum acceptable threshold value for maximum power output has been met by the power input unit for the complete duration of the preceding maximum power output period duration, such as in one or more consecutive number (n) of cycles or with predetermined frequency.

Training system 200 may include session management module 282 incrementing a peak progression of the minimum acceptable threshold value for maximum power output, responsive to each new peak operation of the power input unit. In embodiments, training system 200 may include session management module 282 increasing at least one of the minimum acceptable threshold value of maximum power output and maximum power output duration of the power period. In embodiments, training system 200 may include session management module 282 iterating the increasing of at least one of the minimum acceptable threshold value of maximum power output and maximum power output duration of the power period.

In embodiments, training system 200 may include the session management module 282 configured to determine maximal power period prompts and resting period prompts, and to determine duration of resting periods, in relation to generating and presenting by the processor, via the interface, a prompt or a series of spaced prompts including maximum effort period prompts and resting period prompts that are timed, spaced apart, and determined by reference to a physical conditioning model. In embodiments, training system 200 may include the session management module 282 accessing a physical conditioning model 289. The physical conditioning model 289 may include information from operation records of a pedal-crank input unit, flywheel machine, or both, which operated during the performing of a training method in a previous training session. The physical conditioning model 289 also may include information from referencing physiological response records for the performing of a training method in a previous training session. In an embodiment, the physical conditioning model 289 may include information from operations records of a pedal-crank input unit, flywheel machine, or both, and also from referencing physiological response records. The physical conditioning model 289 may include information from referencing operation records, and physiological response records, in a plurality of operation records for multiple training sessions for a plurality of individuals, or for an individual user.

Training system 200 may include the session management module 282 accessing a physical conditioning model 289 to perform model-based prompting, by generating and presenting by the processor, via the interface, a prompt or a series of spaced maximum effort period prompts and resting period prompts that are timed, spaced apart, and determined by reference to the physical conditioning model. In embodiments, the physical conditioning model 289 may be selected, determined or constructed by reference to operation records for performing a training method in a previous training session, or may be compiled by reference to a plurality of operation records for multiple training sessions. In embodiments, the physical conditioning model 289 may be selected, determined or constructed by reference to operation records of a pedal-crank input unit, flywheel machine, or both, which operated during the performing of the same training method in a previous training session. In some embodiments, the physical conditioning model 289 may be selected, determined or constructed by reference to operation records of a pedal-crank input unit, flywheel machine, or both, which operated during the performing of the same training method by the same individual user in a previous training session. In some embodiments, the physical conditioning model 289 may be selected, determined or constructed by reference to a plurality of operation records of a pedal-crank input unit, flywheel machine, or both, which operated during the performing of the same training method by a plurality of individual users in a previous training session. In embodiments, the session management module 282 may access the physical conditioning model 289 to perform model-based prompting to provide the spaced prompts in correspondence with model values of a physical conditioning model 289 or physiological response model, and may determine such prompts in relation to the physical conditioning model 299 for model values for stimulating maximal activation of a muscle and nervous system of a model person. It will be understood that the physical conditioning model 289 or physiological response model, for example, may relate to a composite model determined for a plurality of individuals, or a model of a particular individual user.

In an embodiment, training system 200 may include, the session management module 282 accessing the physical conditioning model 289 or physiological response model, which may include a range model for training a set of exercising muscles throughout a range of the force (torque) vs. velocity curve for the pedal-crank input unit or flywheel machine. The range model may include a model for operating the pedal-crank input unit or flywheel machine, beginning from a dead stop and accelerating to a maximum RPM value. The range model may include a model for accelerating the pedal-crank input unit or flywheel machine through a range of low velocities (e.g.; 0-60 RPM) where torque is relatively high and demands strength in relation to the physical conditioning model 289 or physiological response model. In an embodiment, the range model may include a model for accelerating the pedal-crank input unit or flywheel machine from a range of low velocities (e.g.; 0-60 RPM) through a range of mid-range velocities (60-150 RPM). A maximal power event or point may be identified in the mid-range velocities (60-150 RPM). Such a maximal power event or point may be identified in relation to the physical conditioning model 289 or physiological response model, as being significant for muscle development in relation to an individual or in relation to a model person. In an embodiment, the range model may include a model for accelerating the pedal-crank input unit or flywheel machine from a range of mid-range velocities (60-150 RPM) into or through a range of high velocities (e.g.; above 150 RPM). A maximal speed event or point may be identified in the range of high velocities (e.g.; above 150 RPM). Such a maximal speed event may be identified in a relation to a physical conditioning model 289 or physiological response model, as being significant for development of coordination in relation to an individual user or in relation to a model person. At velocities above 150 RPM, maximal speed may be achieved, which may serve improved coordination. In an embodiment, in training system 200 a single short sprint or maximal effort period may train exercised muscles for strength, power and coordination, in relation to a physical conditioning model 289 or physiological response model, or in relation to an individual user. In an embodiment, training system 200 may include the session management module 282 accessing the physical conditioning model 289 or physiological response model to perform modeling, wherein the physical conditioning model 289 or physiological response model includes a range model accessed to provide a range of resting period durations for training to stimulate cardiovascular adaptations. Such cardiovascular adaptations may have been previously thought possible only with long duration low intensity exercise (e.g.; running or cycling>30 min at 60-75% maximal oxygen consumption, $VO_2max$). In an embodiment, training system 200 may be a form of 'high intensity interval training' (i.e.; HIIT). In embodiments, training system 200 may embody the highest possible type of HIIT, because the individual user may be prompted to provide maximum exertion in a sprint for a maximum power period having duration from 1-10 seconds of sprinting. In an embodiment, training system 200 may include the session management module 282 accessing the physical conditioning model 289 or physiological response model, wherein in a maximum power period the individual user may cause the pedal-crank input unit to operate and generate power that is 3-6 times higher than power that elicits $VO_2max$ in the physical conditioning model 289 or physiological response model, or for an individual user. In an embodiment, in the physical conditioning model 289 or physiological response model, or for an individual user, a modeled condition or actual condition may exist wherein, in order for the exercised muscles to recover energy stores after a maximal power period, the cardiovascular system may be stimulated to increase oxygen delivery and utilization by the muscles, by increasing heart rate and blood flow. In an embodiment, for example, in the physical conditioning model 289 or physiological response model, or for an individual user, a modeled condition or actual condition may exist wherein two (2) minutes duration of a resting period of may be sufficient for recovery with relatively low stress on the cardiovascular system. In an embodiment, training system 200 may include, in the physical conditioning model 289 or physiological response model, or for an individual user, a modeled condition or actual condition may exist wherein, progression reducing of resting period durations from, for example, 60 seconds, 45 seconds, 30 seconds, to 15 seconds, may place or may be determined to correspond to relatively more stress on the cardiovascular system as measured by grade increases in oxygen consumption, heart rate and muscle oxygen desaturation in the physical conditioning model 289 or physiological response model, or for an individual user. In an embodiment, by accurately controlling the resting period durations between the series of maximal effort periods, it may be possible to stimulate the cardiovascular system to provide significant aerobic improvements. In embodiment, such improvement may be achieved with only 15 minutes of total time for each training session that involves only 1-2 minutes of actual exercise. For example, if a person performs in maximum effort periods each having a duration of 4 seconds, and each of the maximum effort periods is separated by a resting period having a 30 second duration for recovery between maximum effort periods, in a 15 minute training session the individual user will have performed 26 maximum effort periods with combined duration of 104 seconds. In embodiments, training system 200 may be progressive in reduction of resting period durations in relation to the physical conditioning model 289 or physiological response model, or for an individual user, to provide conditions corresponding to relatively more stress on the cardiovascular system as measured by grades increases in oxygen consumption, heart rate and muscle oxygen desaturation in the physical conditioning model 289 or physiological response model, or for an individual user, and thus improve aerobic conditioning. In embodiments, training system 200 may provide progressive improvement of muscular performance with increasing maximal power events or points, and progressive improvement of cardiovascular performance over period of multiple training sessions in relation to progressively shorter resting period durations between maximal power periods (i.e.; progressively reduced from 60, 45, 30 and to 15 seconds) according to the physical conditioning model 289 or physiological response model, or for an individual user.

Training method 10 may be viewed as a training program based on maximal acceleration of an inertial load of a flywheel machine driven by continuous cyclical rotation of a pedal-crank input unit. The pedal-crank input unit may receive maximal power input during a maximal power period, from an individual providing maximal effort throughout a maximal power period that lasts 1-10 seconds depending on the inertia of the flywheel machine and the individual's capacity to deliver power to the pedal-crank input unit. In an embodiment, maximal effort may include a maximum rate of acceleration of the flywheel machine inertial load during a maximum power period. In an embodiment, maximal effort may include a rate of acceleration of the flywheel machine inertial load that is at least equal to or exceeds a minimum acceptable threshold value established from a reference record of power output information from operation of one of a reference pedal-crank input unit and reference flywheel machine in a previous training event. In an embodiment, such a training method may include, after issuance of a maximum power prompt in each maximal power period, during the duration of the maximal power period the pedal-crank input unit receiving from exertion of the individual user, initial maximal power provided by high exertion of muscular strength to accelerate the pedal-crank power input unit driving rotation of the flywheel inertial load from, for example, 0-60 RPM, then maximal high power provided to continue accelerating the flywheel machine inertial load up to 100-120 RPM, and then maximal high speed to achieve highest pedal-crank power and velocity input unit of power to drive the flywheel inertial load.

In embodiments, training system 200 may include the pedal-crank input unit being loaded solely by inertia of a freewheeling flywheel machine (e.g.; angular mass). In an embodiment, the flywheel machine may include the rotatable flywheel and a set of trained gears, where the set of trained gears is drivingly connected between the pedal-crank input unit and rotatable flywheel and provides a gear ratio. In an embodiment, for example, the gear ratio may be 4:1. In embodiments, training system 200 may omit sources of external resistance such as, for example, external mechanical friction, magnetic brakes or motors. In embodiments, for training system 200, instantaneous cycling power may be calculated from the inertia (I) and velocity ($\omega$) and acceleration ($\alpha$) of the flywheel machine (according to the equation Power=I×$\alpha$×$\omega$). An advantage of cycling exercise is that smooth acceleration may be achieved as energy input from the pedal-crank input unit is directed into driving rotation of the freewheeling flywheel. It may be advantageous that, in embodiments having such a freewheeling flywheel, chance of muscle injury is reduced and low relative to exercise modes that may place opposite direction loads on muscles of the user due to reversal of loading in the training equipment or due to discontinuous movement. In embodiments including a freewheeling flywheel, instantaneous and average power can be measured extremely accurately (i.e.; ±>0.8% for ergometer; ±>1.4% for subject). This may provide immediate operation or performance information for the individual user.

In an embodiment, training system 200 may enable an individual user to safely exert maximal effort to smoothly accelerate the freewheeling flywheel in a very short exercise period having a duration of only 1-10 seconds for each maximum power period. This may be viewed as a training program based on maximal acceleration of a freewheeling flywheel machine by operation of a pedal-crank input unit driving rotation of the flywheel. In embodiments, an individual user may exert maximal effort throughout a maximal power period.

Training methods and training systems in exemplary embodiments are described and illustrated. Although specific embodiments are illustrated and described herein, it will be appreciated by those of ordinary skill in the art that any arrangement that is calculated to achieve the same purposes can be substituted for the specific embodiments shown. This application is intended to cover any adaptations or variations of the embodiments and disclosure. For example, although described in terminology and terms common to the field of art, exemplary embodiments, systems, methods and apparatus described herein, one of ordinary skill in the art will appreciate that implementations can be made for other fields of art, systems, apparatus or methods that provide the required functions.

In particular, one of ordinary skill in the art will readily appreciate that the names of the methods and apparatus are not intended to limit embodiments or the disclosure. Furthermore, additional methods, steps, and apparatus can be added to the components, functions can be rearranged among the components, and new components to correspond to future enhancements and physical devices used in embodiments can be introduced without departing from the scope of embodiments and the disclosure. One of skill in the art will readily recognize that embodiments are applicable to future systems, future apparatus, future methods, and different materials.

Terminology used in the present disclosure is intended to include all environments and alternate technologies that provide the same functionality described herein.

What is claimed is:

1. A training method for operating a training system including a pedal-crank input unit in a training event, the pedal-crank input unit drivingly connected in freewheeling relationship to a flywheel machine for outputting power to accelerate a flywheel machine inertial load of at least (0.5) kg·m$^2$, the training system including an ergometer system operable to determine instantaneous power output of the pedal-crank input unit for accelerating the flywheel machine inertial load, the training system including a processor in communication with a display unit, said method comprising:
    associating, by the processor, for the training event, a reference machine operation profile record for one of the pedal-crank input unit and the flywheel machine, said reference machine operation profile record including a reference record of power output information from operation of one of a reference pedal-crank input unit and reference flywheel machine;
    determining, by the processor, from said reference machine operation profile record, an instantaneous maximum power output;
    establishing, by the processor, a minimum acceptable threshold value of maximum power output in relation to the instantaneous maximum power output;
    determining, by the processor, a maximum power output period duration in relation to the instantaneous maximum power output;
    measuring, by said ergometer system, instantaneous power output over time during the duration of the maximum power period, of one of said pedal-crank input unit and said flywheel machine;
    issuing, by the processor, a maximum power prompt in relation to initiating a maximum power period; and
    issuing, by the processor, a resting period prompt in relation to initiating a resting period.

2. The method of claim 1, said method comprising:
    issuing, by the processor, an outcome-dependent prompt in relation to maximum power output measured during the maximum power period.

3. The method of claim 1, said method comprising:
    power finding, by the processor, whether maximum power output measured during the maximum power period at least equals the minimum acceptable threshold value for the same maximum power period.

4. The method of claim 3, said method comprising:
    incrementing, by the processor, in relation to said power finding, the minimum acceptable threshold value of maximum power output in a next power period, where said power finding determines that maximum power output measured during the maximum power period at least equals the minimum acceptable threshold value for the same maximum power period.

5. The method of claim 3, said method comprising:
    issuing, by the processor, an outcome-dependent prompt in relation to said power finding.

6. The method of claim 5, said method comprising:
    said outcome-dependent prompt being a success prompt, where said power finding determines that maximum power output measured during the maximum power period at least equals the minimum acceptable threshold value for the same maximum power period.

7. The method of claim 5, said method comprising:
said outcome-dependent prompt being a failure prompt, where said power finding determines that maximum power output measured during the maximum power period is less than the minimum acceptable threshold value for the same maximum power period.

8. The method of claim 1, said method comprising:
iterative issuing, by the processor, a next maximum power prompt in relation to initiating a next maximum power period;
iterative issuing, by the processor, a next resting period prompt in relation to initiating a next resting period.

9. The method of claim 8, said method comprising:
iterative establishing, by the processor, a next minimum acceptable threshold value of maximum power output for the next maximum power period;
measuring, by said ergometer system, a instantaneous power output over time during the duration of the next maximum power period.

10. The method of claim 8, said method comprising:
modeling a physiological condition, by the processor accessing a physical conditioning model;
wherein said modeling determines at least one of the following:
time of said next resting period prompt,
duration of said next resting period,
time of starting said next resting period, and
time of ending said next resting period.

11. The method of claim 1, said method comprising:
said inertial load in the range of $(0.5)$ kg·m$^2$ to $(10)$ kg·m$^2$.

12. A training system configured to perform the method of any one of claims 1, 2, 3, 4, 5, 6, 7, 8, 9, 10 and 11.

13. A training system for operation in a training event, said training system comprising:
a pedal-crank input unit drivingly connected in freewheeling relationship to a flywheel machine for outputting power to accelerate a flywheel machine inertial load of at least $(0.5)$ kg·m$^2$;
an ergometer system operable to determine instantaneous power output of the pedal-crank input unit when accelerating the flywheel inertial load;
a display unit having an interface;
a processor in communication with said display unit;
a profile module, executable by the processor;
a training session management module, executable by the processor;
at least one of said profile module and said training session management module configured to:
associate, by the processor, for the training event, a reference machine operation profile record for one of the pedal-crank input unit and the flywheel machine, said reference machine operation profile record including a reference record of power output information from operation of one of a reference pedal-crank input unit and reference flywheel machine;
determine, by the processor, from said reference machine operation profile record, an instantaneous maximum power output;
establish, by the processor, a minimum acceptable threshold value of maximum power output in relation to the instantaneous maximum power output;
determine, by the processor, a maximum power output period duration in relation to the instantaneous maximum power output;
issue, by the processor, a maximum power prompt in relation to initiating a maximum power period;
issue, by the processor, a resting period prompt in relation to initiating a resting period;
and
said ergometer system configured to measure instantaneous power output over time during the duration of the maximum power period, of one of said pedal-crank input unit and said flywheel machine.

14. The training system of claim 13, comprising:
the processor issuing an outcome-dependent prompt in relation to maximum power output measured during the maximum power period.

15. The training system of claim 13, comprising:
the processor finding whether maximum power output measured during the maximum power period at least equals the minimum acceptable threshold value for the same maximum power period.

16. The training system of claim 15, comprising:
the processor incrementing, in relation to said finding, the minimum acceptable threshold value of maximum power output in a next power period, where said finding determines that maximum power output measured during the maximum power period at least equals the minimum acceptable threshold value for the same maximum power period.

17. The training system of claim 15, comprising:
the processor, in relation to said finding, issuing an outcome-dependent prompt.

18. The training system of claim 17, comprising:
said outcome-dependent prompt being a success prompt, where said finding determines that maximum power output measured during the maximum power period at least equals the minimum acceptable threshold value for the same maximum power period.

19. The training system of claim 17, comprising:
said outcome-dependent prompt being a failure prompt, where said finding determines that maximum power output measured during the maximum power period is less than the minimum acceptable threshold value for the same maximum power period.

20. The training system of claim 13, comprising:
the processor iterating issuance of a series of a next maximum power prompt in relation to initiating a next maximum power period;
the processor iterating issuance of a series of a next resting period prompt in relation to initiating a next resting period.

21. The training system of claim 20, comprising:
the processor iterating issuance of a series of a next minimum acceptable threshold value of maximum power output for the next maximum power period.

22. The training system of claim 20, comprising:
modeling a physiological condition, by the processor accessing a physical conditioning model;
wherein said modeling determines at least one of the following:
time of said next resting period prompt,
duration of said next resting period,
time of starting said next resting period, and
time of ending said next resting period.

23. The training system of claim 13, comprising:
said inertial load in the range of $(0.5)$ kg·m$^2$ to $(10)$ kg·m$^2$.

* * * * *